United States Patent [19]

Ahr et al.

[11] Patent Number: 5,578,344
[45] Date of Patent: Nov. 26, 1996

[54] PROCESS FOR PRODUCING A LIQUID IMPERMEABLE AND FLUSHABLE WEB

[75] Inventors: Nichholas A. Ahr, Cincinnati; Raymond J. Dirk, Cleves, both of Ohio

[73] Assignee: The Procter & Gable Company, Cincinnati, Ohio

[21] Appl. No.: 561,720

[22] Filed: Nov. 22, 1995

[51] Int. Cl.$^6$ ............................................. B05D 1/00
[52] U.S. Cl. .................... 427/211; 427/411; 427/428; 427/434.4; 427/439
[58] Field of Search ........................... 427/211, 428, 427/434.4, 439, 411

[56] References Cited

U.S. PATENT DOCUMENTS

| | | | |
|---|---|---|---|
| 3,078,849 | 2/1963 | Morse | 128/290 |
| 3,407,814 | 10/1968 | George et al. | 128/290 |
| 3,510,587 | 5/1970 | Marder et al. | 128/284 |
| 3,542,028 | 11/1970 | Beebe et al. | 128/290 |
| 3,561,447 | 2/1971 | Alexander | 128/290 |
| 3,636,952 | 1/1972 | George | 128/287 |
| 3,665,923 | 5/1972 | Champaigne, Jr. | 128/290 W |
| 3,683,919 | 8/1972 | Ells | 128/290 W |
| 3,950,578 | 4/1976 | Laumann | 427/378 |
| 3,967,623 | 7/1976 | Butterworth et al. | 128/287 |
| 3,994,771 | 11/1976 | Morgan, Jr. et al. | 162/113 |
| 4,102,737 | 7/1978 | Morton | 162/113 |
| 4,141,772 | 2/1979 | Buell | 156/227 |
| 4,628,857 | 12/1986 | Coningsby | 118/406 |
| 4,940,513 | 7/1990 | Spendel | 162/112 |
| 5,026,363 | 6/1991 | Pratt | 604/385.1 |
| 5,102,597 | 4/1992 | Roe et al. | 264/126 |
| 5,116,563 | 5/1992 | Thomas et al. | 264/167 |
| 5,190,533 | 3/1993 | Blackburn | 604/367 |
| 5,207,662 | 5/1993 | James | 604/385.2 |
| 5,300,358 | 4/1994 | Evers | 428/286 |
| 5,384,189 | 1/1995 | Kuroda et al. | 428/288 |
| 5,405,342 | 4/1995 | Roessler | 604/364 |
| 5,415,643 | 5/1995 | Kolb | 604/367 |
| 5,417,679 | 5/1995 | Toms et al. | 604/370 |
| 5,431,643 | 7/1995 | Ouellette et al. | 604/385.1 |
| 5,454,801 | 10/1995 | Lauritzen | 604/378 |

FOREIGN PATENT DOCUMENTS

| | | |
|---|---|---|
| 7-03699 | 1/1995 | Japan . |
| 282447 | 5/1928 | United Kingdom . |
| WO93/19715 | 10/1993 | WIPO . |
| WO95/03361 | 2/1995 | WIPO . |
| WO95/16474 | 6/1995 | WIPO . |
| WO95/18191 | 7/1995 | WIPO . |
| WO95/30049 | 11/1995 | WIPO . |

*Primary Examiner*—Bernard Pianalto
*Attorney, Agent, or Firm*—Larry L. Huston; E. Kelly Linman; Jacobus C. Rasser

[57] ABSTRACT

A process for impregnating a resin into a substrate to form a web. The resin is impregnated into one side of the web, so that the other side remains exposed. This arrangement allows the exposed side of the web to be dispersible in water, while the impregnated side is water resistant. The impregnation may occur in zones and comprise one material or two or more materials. The resulting web is useful as a backsheet in disposable absorbent articles wherein it is desired to have a barrier that is impermeable to body fluids, yet flushable for disposal.

20 Claims, 2 Drawing Sheets

PROCESS FOR PRODUCING A LIQUID IMPERMEABLE AND FLUSHABLE WEB

FIELD OF THE INVENTION

The present invention relates to a disposable absorbent article, such as a diaper, sanitary napkin, panty liner, incontinence pad, or the like. More particularly, the present invention is directed to a process for producing a water dispersible and flushable web for use in such a disposable absorbent article.

BACKGROUND OF THE INVENTION

Disposable absorbent articles are well known in the art and have been commercially available for many years. Typically, a disposable article comprises a liquid pervious topsheet, a liquid impervious backsheet joined with the topsheet, and an absorbent core between the topsheet and the backsheet. The backsheet typically comprises a liquid impermeable material. Furthermore, the backsheet must be thin and flexible for comfort.

A long-felt need has existed for more convenient and discreet disposal methods for such absorbent articles, particularly for sanitary napkins and the like. One method that would provide such improved convenience and discretion is the use of a conventional toilet for such disposal. The core is easily made flushable. Likewise, a topsheet which does not comprise a formed film can be made flushable. Because the backsheet is liquid impermeable, there is a substantial risk of disposal problems, such as clogging, if commercially available sanitary napkins and similar disposable absorbent articles are disposed of by flushing down a conventional toilet. One way of resolving this problem is to provide a backsheet that would be both liquid impermeable and flushable.

A number of attempts have been made to provide flushable absorbent articles with flushable backsheets.

For example, British Patent No. 282,447 attempts a partial solution by providing a core said to be flushable and a repellent treated barrier which is separated from the core and needs to be disposed of by other means. U.S. Pat. No. 3,078,849, issued to Morse on Feb. 26, 1962, describes a sanitary napkin incorporating a fluid sensitive, temporary barrier within the absorbent core for spreading bodily fluids but makes no provision for a water sensitive outer coveting. U.S. Pat. No. 3,561,447, issued to Alexander on Mar. 13, 1969, describes a sanitary napkin having a nonwoven fabric covering wherein the nonwoven fabric comprises textile length fibers and a binder for the nonwoven having a combination of a soft acrylic binder and polyvinyl alcohol. This combination is said to have sufficient strength when damp to serve as an outer covering while still dispersing in water under mild agitation. While such a structure may have wet strength, it is unlikely that it will have sufficient barrier properties to be a satisfactory backsheet for a modem sanitary napkin. U.S. Pat. No. 3,665,923, issued to Champaigne, Jr. on May 30, 1972, describes a sanitary napkin with a wrapper comprising a nonwoven fiber web that is bonded by a water dispersible adhesive such as polyvinyl alcohol. A preferred embodiment also comprises a baffle member of a thin impervious plastic film interposed between the absorbent pad and the wrapper. This structure solves the problem of providing barrier properties by providing a non-dispersible member with the requisite barrier properties. Repeated flushing of such structures poses the risk of clogging sewer pipes because the baffle member will not disperse into small particles. U.S. Pat. No. 5,300,358, issued to Evers on Apr. 5, 1994 describes the absorbent structures wherein the backsheet comprises two sheets of polyvinyl alcohol film with a highly absorbent paper structure therebetween. All surfaces that may be exposed to aqueous fluids are treated with a water repellent material, such as a fluorocarbon. The absorbent structure is also provided with a tear strip or string which, when pulled at disposal, is said to expose the highly absorbent paper structure to water which then wicks the water to the non-repellent treated surfaces so they can dissolve. The requirement of a tear strip is an obvious inconvenience.

One particular attempt to resolve the problem has been to use a backsheet having a flushable substrate coated with a substrate having the necessary barrier properties and being compostable when flushed. An example of such an attempt is illustrated in commonly assigned U.S. Pat. No. 5,417,679, issued May 23, 1995 to Toms et al., which patent is incorporated herein by reference.

U.S. Pat. No. 5,116,563, issued to Dennis A. Thomas et al, on May 26, 1992, describes a process not having matched velocities, but useful for forming mechanical fastening prongs by depositing a heated resinous material onto a substrate. The substrate is transported at a speed from approximately 25% greater than to approximately 15% less than the speed of a roll depositing the resinous material. This process, however, does not produce a thin, uniform and flexible coating of a resin on a substrate.

Thus, it is an object of the present invention to provide a process for producing a uniform, thin and flexible web that is liquid impermeable and yet water dispersible, and which can be used in flushable disposable absorbent articles. It is a further object of the present invention to provide a process for producing a uniform, thin and flexible web that readily disperses into small portions when exposed to water and thereby is disposable by flushing a conventional toilet. It is still another object of the present invention to provide a process for producing a liquid impermeable web from a water permeable substrate, said impermeable web having a greater tensile strength than the substrate, without increasing the caliper of the substrate.

BRIEF SUMMARY OF THE INVENTION

The invention comprises a process for producing a liquid impermeable and flushable web. The process comprises the steps of providing a flowable resinous material and applying this resinous material to a substrate.

The substrate is transported at a transport velocity, relative to a printing roll and a corresponding anvil, through the nip defined by the printing roll and the anvil. The printing roll, having a plurality of cells disposed about its periphery, is axially rotated at a peripheral velocity. The flowable resinous material is transported to the printing roll, thereby the flowable resinous material is deposited into the cells of the printing roll. The substrate is transported in contacting relation with the cells of the roll. The flowable resinous material is applied from the cells of the roll onto the substrate. The peripheral velocity of the printing roll is at least about 100% greater than the transport velocity of the substrate. This velocity differential causes the printing roll to wipe the flowable resinous material onto and into the substrate, creating thereby even and uniform application of the resinous material thereon. The wiping process created by the velocity differential causes the resinous material to penetrate into the substrate, a process which a conventional rotary printing does not provide. This penetration of the resinous material into the substrate causes the substrate to become water impermeable, enhances the tensile strength of the resulting web and prevents the increase of the caliper (and hence mitigates a decrease in flexibility) of the resulting web.

In a different execution, the process for producing a liquid impermeable and flushable web comprises two coating steps, a first coating step and a second coating step which may be performed in substantially the same manner as the first coating step. A two step coating process is preferable because the two step coating process causes impermeability of the resulting web at a lower overall level of applied resinous material than would be required for equivalent impermeability using a single step coating process. A velocity differential at the second coating step may be equal to, less or greater than the velocity differential at the first coating step.

In another embodiment of the invention, the coating performed at the first coating step and the coating performed at the second coating step are applied to the mutually opposed sides of the substrate.

In still another embodiment of the present invention, the first resinous material is applied by the first coating step and a different second resinous material is applied by the second coating step.

In still another embodiment of the present invention, the coating performed at the first coating step and the coating performed at the second coating step are applied at different coating widths. The different widths may be oriented in either the machine direction or the cross machine direction.

Cooling air may be provided after each coating step to insure that the resinous material has solidified, if such cooling is necessary for process hygiene.

BRIEF DESCRIPTION OF THE DRAWINGS

While the Specification concludes with claims particularly pointing out and distinctly claiming the present invention, it is believed the invention is better understood from the following description taken in conjunction with the associated drawings, in which like elements are designated by the same reference numeral and:

DETAILED DESCRIPTION OF THE INVENTION

The invention comprises a process for producing a water dispersible, liquid impermeable web. As used herein a "web" is a macroscopically planar substrate, impregnated with a flowable, resinous material. The resinous material may be deposited onto the substrate in liquid form.

Figure 1:
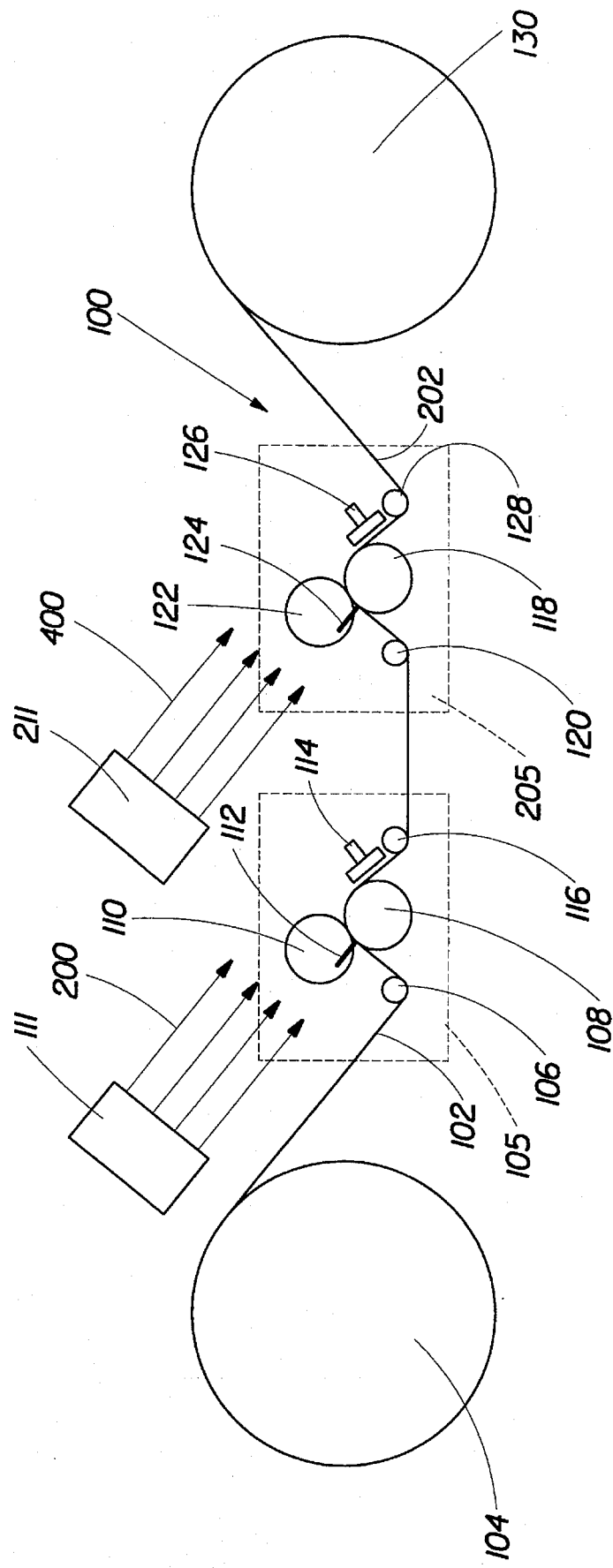
FIG. 1 is a schematic side elevational view of an apparatus for producing a web according to the present invention coated on one side.

Referring to FIG. 1, the process for producing a liquid impermeable and flushable web comprises the following steps. The substrate 102, having a first side and a mutually opposed second side, is unwound from a parent roll 104. The substrate 102 is fed to a first printing station 105 comprising a first backing anvil 108, a first printing roll 110, and a first feed roll 106. The first backing anvil 108 is juxtaposed with the first printing roll 110 to form a first nip therebetween.

The first printing roll 110 has a plurality of cells disposed about its periphery. In a preferred embodiment, the first backing anvil 108 comprises a first backing roll rotatable about its longitudinal axis. After being heated to the melting point, or otherwise treated, the resinous material 200 is delivered to the first printing roll 110 by a first delivery mechanism 111. The resinous material 200 is then applied to and impregnated with the substrate 102.

Tension control devices and tracking devices (not shown) well known in the art may also be used in this process, if such devices are necessary to insure an even coating of the resinous material 200 across the entire transverse width of the substrate 102.

A resinous material 200 is provided in a liquid state. If the resinous material 200 is in a solid state at room temperature, it may be heated to a temperature above its melting point. Alternatively, resinous materials in a liquid state at room temperature may also be used. For example, prepolymers comprising chemically reactive end groups may be utilized. In this case, after depositing the resinous material 200 onto and into the substrate 102, a subsequent curing step is necessary to convert a resinous material 200, such as a liquid prepolymer, into the solid state. Actinic radiation is suitable.

In the preferred embodiment of the process, a first resinous material 200 is heated to at least its melting point, causing the resinous material 200 to be flowable.

The substrate 102 is transported, at a transport velocity, relative to the first printing roll 110 and the first backing anvil 108, through the first nip defined by the first printing roll 110 and the first backing anvil 108. The flowable first resinous material 200 is disposed into the cells of the first printing roll 110. The substrate 102 is transported through the first nip in contacting relation with the cells of the first printing roll 110. The first printing roll 110 rotates about its first longitudinal axis at a first peripheral velocity, thereby applying the flowable first resinous material 200 from the cells of the first printing roll 110 onto the substrate 102. Preferably, the coating weight of the first resinous material 200 on the substrate 102 is between about 0.005 grams per square inch and about 0.075 grams per square inch. More preferably, the coating weight is between 0.015 and 0.035 grams per square inch.

While rotary printing processes are well known in the art, the process described and claimed herein differs from such known processes in that during the process of applying the flowable first resinous material 200 onto the substrate 102 according to the present invention, a first velocity differential occurs between the transport velocity of the transported substrate 102 and the peripheral velocity of the first printing roll 110. The first peripheral velocity of the first printing roll is at least about 100% greater than the transport velocity of the substrate 102, so that the first velocity differential occurs. The term "velocity differential" is defined herein as (peripheral velocity−transport velocity)/transport velocity×100%. Preferably, the first velocity differential ranges from about 100% to about 500%. More preferably, the first velocity differential ranges from 300% to 350%.

This first velocity differential causes the first print roll 110 to wipe the first resinous material 200 onto and into the substrate 102 in a shearing action and thereby creates an even and uniform application of the first resinous material 200 therein, such that the resinous material 200 penetrates the substrate 102 and occupies the interstitial spaces and voids of the substrate 102. Such wiping application under shear stress prevents the caliper of the substrate from increasing when the first resinous material 200 is applied thereto. Caliper is measured with a caliper gauge, Model 65.503, supplied by Ono Sokki Co. of Japan, using a 0.95 inch diameter presser foot and a confining pressure of 0.1 psi.

As noted above, the wiping process created by the first velocity differential causes the first resinous material 200 to penetrate deeper into the substrate 102 than a conventional rotary printing process allows. By way of non-limiting example, a through air dried paper having apertures measuring 3.5 millimeters×1.5 millimeters and a caliper of 0.5 millimeters was impregnated with resin according to the present invention as described below. After the doctoring process, the resin in the apertures was measured to have a thickness ranging from 0.10 millimeters to 0.34 millimeters. Interestingly, the resinous material 200 occurred on the face of the web 202 contacting the backing anvil 108. The first side of the web 202 oriented towards the printing roll 110 and doctor blade 112 was generally free of the resinous material 200. The depth of the resin was measured, for this example, using a digital Vernier micrometer having pointed opposing tips with a footprint of less than 1 square millimeter. One of the tips rested on a balance so the confining force could be measured. The thickness of the resinous material 200 in the apertures of the web 202 was measured at a confining force between 0.01 and 1.00 grams. These readings were confirmed with a non-contacting laser displacement center having a visible beam measuring 1 millimeter×2 millimeters.

Such penetration of the first resinous material 200 into the substrate 102 causes the resulting web 202 to become liquid impermeable without increasing the caliper of the substrate 102. In addition, this penetration of the resinous material 200 into the substrate 102 enhances the tensile, shear, burst and tear strengths of the resulting web 202. The tensile strength of the resulting web 202 is at least 2 times as great as the tensile strength of a like substrate having the same caliper as the resulting web.

With continuing reference to FIG. 1, the process according to the present invention may utilize a variety of types of printing rolls 110, including, but not limited to a screen printing roll and a Gravure printing roll. In a preferred embodiment of the claimed invention, a screen printing roll is used. A screen printing roll is well known in the art, as illustrated by U.S. Pat. No. 4,628,857, issued Dec. 16, 1986 to Coningsby, and incorporated herein by reference. Gravure printing rolls are also well known in the an as illustrated by U.S. Pat. No. 4,634,130, issued Feb. 17, 1988, to Sheath et al. and incorporated herein by reference to illustrate the general state of the art.

A screen printing roll 110 is selected. The thickness of the screen is preferably from 0.002 to 0.007 inches. Preferably, a 50 mesh nero screen is used having 50×50 cells per square inch. The cells may measure 0.0035 inches across the flats and be oriented at a 20 degree angle relative to the circumferential direction of the print roll 110. If desired, a chrome plated honeycomb screen may be utilized for strength, particularly if a fine mesh size is desired.

The areas of either the gravure printing roll 110 or screen printing roll 110 from which resin is applied to the substrate 102 is referred to as the printing zone. If desired, the printing roll 110 may have zones which do not print, hereinafter referred to as non-printing zones. The printing zones deposit resinous material 200 onto the substrate 102 only in those regions corresponding to the registration of the printing zones with the substrate 102. Likewise, the areas of the substrate 102 which were registered with the non-printing zones will be relatively, if not completely, free of the resinous material 200.

If a gravure roll is selected for the first printing roll 110, the non-printing zones may simply be smooth areas of the roll which do not contain gravure cells. If a screen printing roll is selected for the first printing roll 110, the screen printing roll may have impermeable bars which block transmission of the first resinous material 200 through the screen at the positions of the bars.

The non-printing zones may be generally longitudinally oriented and parallel to the axis of the printing roll. This arrangement produces generally cross machine direction oriented zones in the substrate 102 which do not contain the first resinous material 200. This arrangement may be utilized if desired to trim the resulting web 202 into individual cores for disposable absorbent articles and the non-printing areas desired to be used for waist margins, etc.

Alternatively, the non-printing zones may be generally circumferentially oriented, resulting in machine direction oriented zones of the substrate 102 not having the resinous material 200 printed thereon. If desired, several repeating units of the web 202 having zones with and without the resinous material 200 may be juxtaposed together to form a resulting web which is relatively wide in the cross machine direction. The resulting web 202 is then cut in the machine direction at positions corresponding to the desired zones to produce roll stock for use in later production. This arrangement provides the benefits of economy of scale in making disposable absorbent articles according to the present invention.

A first doctor blade 112 is used to insure that the first resinous material 200 is evenly metered across the entire application face of the printing roll 110. The first doctor blade 112 is juxtaposed with the first printing roll 110 and held stationary as it is rotated, allowing the first doctor blade 112 to wipe the circumference of the first printing roll 110. The first doctor blade 112 scrapes any of the first resinous material 200 not disposed within the individual cells from the first printing roll 110.

The first backing anvil 108 is smooth and can either comprise a rotatable backing roll or a stationary surface. For the embodiment described herein, a rotatable backing roll 108 is selected. The first printing roll 110 and the first backing roll 108 are compressed against each other to provide sufficient frictional engagement and compression between the substrate 102 and the first resinous material 200 in order to promote wiping of the first resinous material 200 onto and into the substrate 102.

If a thermoplastic resin is selected as the first resinous material 200, the first printing roll 110 is preferably heated to prevent premature solidification of the flowable first resinous material 200. A printing roll temperature of about 270° F. has been found to work well with the first resinous material 200 and process conditions described hereunder.

While the substrate 102 is preferably comprised of wet laid tissue, any fibrous substrate that is readily dispersible under mild agitation in cold water is suitable. Suitable fibers include, but are not limited to cotton cellulose and other natural fibers and synthetic fibers, such as polyester, polypropylene, polyethylene, nylon, viscose rayon fibers, cellulose acetate, polyethylene terephthalate and other synthetic fibers or a combination of natural and synthetic fibers. The substrate 102 may also be at least partially comprised of chemically modified natural fibers such as cross-linked cellulose fibers. Suitable cross-linked cellulose fibers are described in U.S. Pat. No. 4,888,093 issued Dec. 19, 1989 to Cook, et al.; U.S. Pat. No. 4,822,543 issued Apr. 18, 1989 to Dean, et al.; U.S. Pat. No. 4,898,642 issued Feb. 6, 1990 to Moore, et al.; U.S. Pat. No. 4,935,022 issued Jun. 6, 1990 to Lash, et al.; U.S. Pat. No. 5,137,537 issued Aug. 11, 1992 and U.S. Pat. No. 5,183,707 issued Feb. 2, 1993 to Herron et al., all of which patents are incorporated herein by reference.

Suitable cellulosic substrates 102 may be made according to commonly assigned U.S. Pat. No. 4,191,609 issued Mar. 4, 1980 and U.S. Pat. No. 4,529,480 issued Jul. 16, 1985 to Paul D. Trokhan, both patents being incorporated herein by reference. A suitable substrate 102 has a basis weight of about 12 pounds per 3000 square feet and is available from Georgia-Pacific Corp. of Bellingham, Wash. under the designation DST-1.

In order to insure easy dispersibility, the fibers of the substrate 102 should either be intrinsically hydrophilic or treated to be hydrophilic. As used therein, a "hydrophilic" material has a contact angle between water and the material surface of less than 90 degrees. Methods of treating fibrous ,assembles are described in U.S. Pat. No. 4,950,2545, issued to Osborn on Aug. 21, 1994, the disclosure of which is incorporated herein by reference.

High internal phase emulsion (HIPE) foams, as described in U.S. Pat. No. 5,147,345, issued to Young, et al. on Sep. 15, 1992, and incorporated herein by reference, are also suitable for use as the substrate 102. HIPE foams provide the additional advantage that they are also capable of absorbing bodily fluids, and can provide at least a portion of the absorbent capacity of the sanitary napkin. In the claimed invention, a preferable first resinous material 200 is a hot melt thermoplastic blend that is available from Century International of Columbus, Ohio, under the designation CA-105.

The first resinous material 200 may be externally heated by known means (not shown) to maintain the material 200 in a liquid state and at the proper temperature and viscosity. Typically, the first resinous material 200 is maintained at a temperature slightly above the melting point. The temperature is considered to be at or above the melting point if the first resinous material 200 is partially or wholly in the liquid state. If the temperature is too low, it may not transfer from the printing roll 110 to the substrate 200, or subsequently, may not be suitable for the wiping process as described above. Conversely, if the temperature is too high, the material 200 may not be viscous enough to be suitable for the wiping process or thermally decompose. However, the temperature should not be so high as to damage the substrate 102. For the embodiments described herein, the preferred temperature of the first resinous material 200 is from about 200° F. (93° C.) to about 250° F. (121° C.) at the point of application to the substrate 102. This temperature is above the melting point of the aforementioned CA-105 resinous material 200 but below that at which a significant loss of viscoclasticity occurs. Cooling air may optionally be provided from a first air cooling system 114. The cooling air may be necessary to insure that the first resinous material 200, already applied to the substrate 102, has solidified before the web 202 is removed from the first printing roll 110 by a first stripping roll 116.

In a preferred embodiment of the invention, a two step coating process is utilized. In a two step coating process, the web 202 may be fed to a second printing station 205 comprising a second backing anvil 118, a second printing roll 122, and a second feed roll 120. A second application of the first resinous material 200 by a second delivery mechanism 211 may then be made using the second printing roll 122 and the second backing anvil 118 in substantially the same manner as described above. Alternatively, a second resinous material 400, different from the first resinous material 200, may be used in the second coating process.

A two step coating process is preferred because it provides greater impermeability of the resulting web 202 at a lower coating weight than an equivalent single step coating process.

The second velocity differential of the second coating step may be equal to, less than or greater than the velocity differential at the first coating step. Preferably, the second velocity differential is equal to the first velocity differential, particularly if the first resinous material 200 is used at both the first and second printing stations 105, 205.

A second cooling air system 126 may be utilized to insure that the first resinous material 200 or the alternative second resinous material 400 applied to the substrate 102 at the second coating step has solidified before the web 202 is removed from the second printing roll 118 by the second stripping roll 116.

The coated web 202 is then removed from the second printing roll 122 by the second stripping roll 128 and wound into a finished roll 130.

Figure 2:
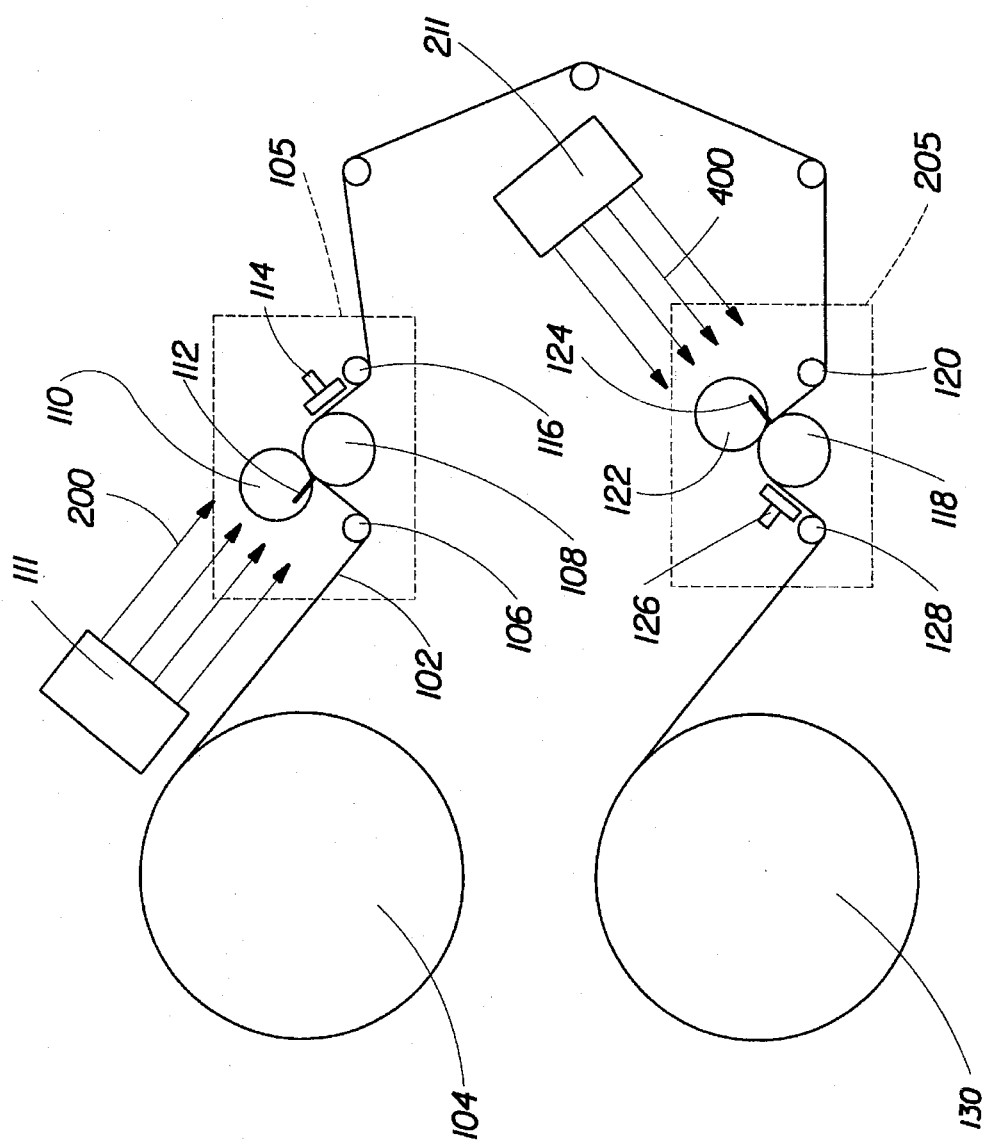
FIG. 2 is a schematic side elevational view of an apparatus for producing a web according to the present invention and coated on opposite sides.

In another embodiment of the invention shown in FIG. 2, the coating applied by the first printing station 105 and the coating applied by the second printing station 205 are applied to the first and second mutually opposed sides of the substrate 102.

When the substrate 102 is coated with the first resinous material 200, using the process described above, the resulting web 202 is impervious to bodily fluids, such as menses and/or urine. Specifically, the web 202 is capable of maintaining, without leakage, a hydrostatic head of preferably at least 12, more preferably at least 15, and even more preferably at least 20 centimeters of water.

Preferably the surface of the web 202 to which the first resinous material 110 is applied, or the second resinous material 210 is applied if such an embodiment is selected, has a critical surface tension of at least 34 dynes per inch when measured using the modified TAPPI test method (T 698 pm-83).

The water resistant resinous material made by the process of the present invention represents an improvement over the hydrophobic materials typically used by the prior art to protect the water sensitive material comprising the backsheet (a typical prior art water sensitive material is poly (vinyl alcohol) and a typical prior art hydrophobic material is a fluorocarbon). Specifically, the hydrophobic materials used by prior art have very low critical surface tensions. For example, the critical surface tension of Teflon® is less than 20 dynes per centimeter (Adamson, A. W., *Physical Chemistry of Surfaces,* 1976, John Wiley & Sons, New York, page 354). The critical surface tension of other fluorocarbon treated surfaces is similar. This low critical surface tension means that assembly of an absorbent article will be made more difficult because a low critical surface tension interferes with adhesive bonding because adhesives will not spread on and adhere to such surfaces (low critical surface tension is also the basis of commercially available anti-stain treatments because stains will not adhere to surfaces having a low critical surface tension). This means there is a need to either ensure that there is no fluorocarbon in areas of adhesive bonding (with the resulting manufacturing complexity of insuring adequate registration of those areas with the remaining components of a sanitary napkin) or to treat any fluorocarbon surface in an area of adhesive bonding to increase the critical surface tension thereof.

A high critical surface tension of the web of the present invention allows utilization of ordinary manufacturing processes to assemble a sanitary napkin using the web coated at one side as a backsheet, without the necessity of additional processing steps.

Thus, as used herein, a water resistant resinous material not only provides a fibrous assembly with a surface that is impervious to bodily fluids but also provides the coated web with a surface suitable for joining to other components using adhesive means (i.e., critical surface tension greater than about 34 dynes per centimeter).

Not only is the web 202 of the present invention impervious to bodily fluids, it also rapidly loses mechanical integrity and dissociates into fragments upon immersion in water. The web 202 loses wet strength and is easily water dispersible because the water resistant resinous material 200 only protects one side of the fibrous substrate from water in the first embodiment. When used as the backsheet of a sanitary napkin, the web 202 has the water resistant resinous material 200 impregnated in the substrate 102 of the web 202 oriented towards those components of the sanitary napkin, such as the absorbent core, that are intended to be wet with bodily fluids. Thus the coating protects the substrate 102 from absorbing bodily fluids while the substrate 102 provides the requisite mechanical integrity.

In an alternative embodiment, the first resinous material 110 or the second resinous material 210 may be deposited onto the substrate 102 by a slot extruder. The substrate 102 and resinous materials 110, 210 are then run through a printing station 105, 205 as described above, so that the resinous materials 110, 210 are impregnated into the substrate 102. Any pair of metering rolls is suitable for such a printing station 105, 205 since the resinous material 110, 210 has already been applied by the slot extruder.

It will be apparent to one skilled in the art that various combinations of the foregoing are feasible. For example, either the first resinous material 110 and second resinous material 210 may be disposed in juxtaposed machine direction oriented printing zones and non-printing zones, or juxtaposed in cross machine direction oriented printing zones and non-printing zones. Alternatively, the first resinous material 110 may be juxtaposed in machine direction oriented printing zones and non-printing zones and the second resinous material 210 be juxtaposed in cross machine direction oriented printing zones and non-printing zones, or vice versa. The printing zones of the first and second resinous materials 110, 210 may comprise the same or different material without regard to the presence, absence or juxtaposition of any non-printing zones.

What is claimed is:

1. A process for producing a liquid impermeable and flushable web, said process comprising the steps of:

providing a water dispersible substrate having a first side and a second side, said sides being mutually opposed;

providing a first resinous material;

heating said first resinous material so that said first resinous material is flowable;

providing a first printing roll having a first longitudinal axis, said first printing roll being rotatable about said first longitudinal axis;

providing a first anvil, said first anvil being juxtaposed with said first printing roll to form a first nip therebetween;

transporting said substrate relative to said first printing roll and said first anvil at a transport velocity;

depositing said first resinous material to said first printing roll;

rotating said first printing roll about said first longitudinal axis at a first peripheral velocity, said first peripheral velocity is at least about 100% greater than said transport velocity, thereby creating a first velocity differential, and applying said first resinous material from said first printing roll to said first side of said substrate, said first resinous material having sheer forces imparted thereto by said velocity differential to impregnate said substrate with said first resinous material, whereby said first resinous material is impregnated into said substrate; and wherein a web is formed from said substrate, said web having a first side, impregnated with said first resinous material.

2. The process according to claim 1, further comprising the steps:

providing a second resinous material which is flowable;

providing a second printing roll having a second longitudinal axis, said second printing roll being rotatable about said second longitudinal axis;

providing a second anvil, said second anvil being juxtaposed with said second printing roll to form a second nip therebetween;

transporting said web relative to said second printing roll and said second anvil at a transport velocity;

depositing said second flowable resinous material to said second printing roll; and rotating said second printing roll about said first longitudinal axis at a second peripheral velocity, said second peripheral velocity is at least about 100% greater that said transport velocity, thereby creating a second velocity differential, and applying said second resinous material from said second printing roll to said first side of said web, said second resinous material having sheer forces imparted thereto by said velocity differential to coat said web with said second resinous material whereby said second resinous material is impregnated into said substrate.

3. The process according to claim 2 wherein said second resinous material is impregnated into the same side of said substrate as said first resinous material is impregnated into.

4. The process according to claim 3, wherein said second velocity differential is equal to said first velocity differential.

5. The process according to claim 2 wherein said second resinous material is impregnated into the opposite side of said substrate as said first resinous material is impregnated into.

6. The process according to claim 2, wherein said second velocity differential is from 200% to 350%.

7. The process according to claim 2, wherein said second resinous material is different from said first resinous material.

8. The process according to claim 2, wherein said second velocity differential is at least 100% greater than said first velocity differential.

9. The process according to claim 2, wherein coating with said first resinous material and coating with said second resinous material are applied at different coating widths.

10. The process according to claim 1, further comprising the steps:

providing a second resinous material which is flowable;

providing a second printing roll having a second longitudinal axis, said second printing roll being rotatable about said second longitudinal axis;

providing a second anvil, said second anvil being juxtaposed with said second printing roll to form a second nip therebetween;

transporting said web relative to said second printing roll and said second anvil at a transport velocity;

depositing said second flowable resinous material to said second printing roll; and rotating said second printing roll about said first longitudinal axis at a second peripheral velocity, said second peripheral velocity is at least about 100% greater that said transport velocity, thereby creating a second velocity differential, and applying said second resinous material from said second printing roll to said second side of said substrate, said second resinous material having sheer forces imparted thereto by said velocity differential to coat said web with said second resinous material.

11. The process according to claim 1, wherein said first velocity differential is from 300% to 350%.

12. The process according to claim 1, wherein said resin is sufficiently impregnated into said substrate so that said web has a caliper not greater than the caliper of said provided substrate.

13. The process according to claim 1, wherein said impermeable flushable web has a tensile strength at least 2 times greater than the tensile strength of said provided substrate.

14. A process for producing a liquid impermeable and flushable web, said process comprising the steps of:

providing a substrate having a first side and a second side, said sides being mutually opposed;

providing a first resinous material which is flowable;

providing a first printing roll having a first longitudinal axis, said first printing roll being rotatable about said first longitudinal axis, said first printing roll having printing zones and non-printing zones;

providing a first anvil, said first anvil being juxtaposed with said first printing roll to form a first nip therebetween;

transporting said substrate relative to said first printing roll and said first anvil at a transport velocity;

depositing said first flowable resinous material to said printing zones of said first printing roll;

rotating said first printing roll about said first longitudinal axis at a first peripheral velocity, said first peripheral velocity being different than said transport velocity, thereby creating a first velocity differential, and applying said first resinous material from said printing zones of said first printing roll to said first side of said substrate, said first resinous material having sheer forces imparted thereto by said velocity differential to impregnate said substrate with said first resinous material, whereby said first resinous material is impregnated into said substrate; and wherein a web is formed from said substrate, said web having a first side impregnated with said first resinous material, at positions registered with said printing zones of said first printing roll.

15. The process according to claim 14, further comprising the steps of providing a second resinous material which is flowable;

providing a second printing roll having a second longitudinal axis, said second printing roll being rotatable about said second longitudinal axis, said second printing roll having printing zones and non-printing zones;

providing a second anvil, said second anvil being juxtaposed with said second printing roll to form a second nip therebetween;

transporting said web relative to said second printing roll and said second anvil at a transport velocity;

depositing said second flowable resinous material to printing zones of said second printing roll; and rotating said second printing roll about said first longitudinal axis at a second peripheral velocity, said second peripheral velocity being different than said transport velocity, thereby creating a second velocity differential, and applying said second resinous material from said printing zones of said second printing roll to said first side of said web, said second resinous material having sheer forces imparted thereto by said velocity differential to coat said web with said second resinous material whereby said second resinous material is impregnated into said substrate.

16. The process for producing the web according to claim 14, wherein said substrate is transported in a machine direction, said process having a cross machine direction orthogonal thereto, wherein the said printed zones impregnated with said first resinous material are juxtaposed in the machine direction.

17. The process for producing the web according to claim 14, wherein said substrate is transported in a machine direction, said process having a cross machine direction orthogonal thereto, wherein said printed zones impregnated with said second resinous material are juxtaposed in the cross machine direction.

18. The process according to claim 14, further comprising the steps:

providing a second resinous material which is flowable;

providing a second printing roll having a second longitudinal axis, said second printing roll being rotatable about said second longitudinal axis, said second printing roll having printing zones and non-printing zones;

providing a second anvil, said second anvil being juxtaposed with said second printing roll to form a second nip therebetween;

transporting said web relative to said second printing roll and said second anvil at a transport velocity;

depositing said second flowable resinous material to said printing zones of said second printing roll; and rotating said second printing roll about said first longitudinal axis at a second peripheral velocity, said second peripheral velocity being different than said transport velocity, thereby creating a second velocity differential, and applying said second resinous material from said printing zones of said second printing roll to said first side of said web, said second resinous material having sheer forces imparted thereto by said velocity differential to coat said web with said second resinous material whereby said second resinous material is impregnated into said substrate.

19. The process for producing the web according to claim 18, wherein said substrate is transported in the machine direction, said process having a cross machine direction orthogonal thereto, wherein said printed zones impregnated with said first resinous material are juxtaposed in the cross machine direction.

20. The process for producing the web according to claim 18, wherein said substrate is transported in a machine direction, said process having a cross machine direction orthogonal thereto, wherein said printed zones impregnated with said second resinous material are juxtaposed in the cross machine direction.

* * * * *

UNITED STATES PATENT AND TRADEMARK OFFICE
CERTIFICATE OF CORRECTION

PATENT NO. : 5,578,344
DATED : November 26, 1996
INVENTOR(S) : Nicholas A. Ahr et al.

It is certified that error appears in the above-indentified patent and that said Letters Patent is hereby corrected as shown below:

Column 1, line 46  delete "coveting" and insert --covering--.
Column 1, line 56  delete "modem" and insert --modern--.
Column 5, line 46  delete "an" and insert --art--.

Signed and Sealed this

Tenth Day of June, 1997

Attest:

BRUCE LEHMAN

Attesting Officer   Commissioner of Patents and Trademarks